United States Patent
Ramsden et al.

(10) Patent No.: US 9,720,111 B2
(45) Date of Patent: Aug. 1, 2017

(54) NEUTRON DETECTOR AND METHOD FOR DETECTING NEUTRONS

(71) Applicant: SYMETRICA LIMITED, Southampton, Hampshire (GB)

(72) Inventors: David Ramsden, Southhampton (GB); Mark Abbott Foster, Southhampton (GB)

(73) Assignee: Symetrica Limited (GB)

( * ) Notice: Subject to any disclaimer, the term of this patent is extended or adjusted under 35 U.S.C. 154(b) by 858 days.

(21) Appl. No.: 14/188,651

(22) Filed: Feb. 24, 2014

(65) Prior Publication Data

US 2017/0184736 A1  Jun. 29, 2017

(30) Foreign Application Priority Data

Feb. 25, 2013 (GB) .................................. 1303245.3

(51) Int. Cl.
*G01T 3/08* (2006.01)
*G01T 3/06* (2006.01)
(Continued)

(52) U.S. Cl.
CPC .............. *G01T 3/06* (2013.01); *G01N 23/09* (2013.01); *G01T 1/2018* (2013.01); *G01T 3/08* (2013.01);
(Continued)

(58) Field of Classification Search
None
See application file for complete search history.

(56) References Cited

U.S. PATENT DOCUMENTS

| | | | | |
|---|---|---|---|---|
| 5,321,269 A | * | 6/1994 | Kitaguchi et al. | 250/370.05 |
| 2005/0133726 A1 | * | 6/2005 | Frankle et al. | 250/390.06 |

(Continued)

FOREIGN PATENT DOCUMENTS

| | | |
|---|---|---|
| GB | 2482024 | 1/2012 |
| GB | 2490513 | 11/2012 |

(Continued)

OTHER PUBLICATIONS

Indinc.com, http://www.indinc.com/products/category/38/; Copyright 2014 Indinc.com; Feb. 19, 2014; This Domain Name May Be for Sale. To Inquire, Call Buydomains.com at 339-222-513; p. 1 of 2.

(Continued)

*Primary Examiner* — David Porta
*Assistant Examiner* — Hugh H Maupin
(74) *Attorney, Agent, or Firm* — Fitzsimmons IP Law

(57) ABSTRACT

An apparatus comprises a neutron detector. The neutron detector comprises a conversion layer comprising a mixture of a neutron absorbing material and a scintillation material; and a photodetector optically coupled to the conversion layer and arranged to detect photons generated as a result of neutron absorption events in the conversion layer; wherein the apparatus is adapted to be carried by a user and the conversion layer is positioned within the neutron detector such that when the apparatus is being carried by a user in normal use neutrons are absorbed in the conversion layer after passing through the user such that the user's body provides a neutron moderating effect. In some cases the apparatus may be carried in association with a backpack or clothing worn by a user, for example, the neutron detector may be sized to fit in a pocket. In other cases the apparatus may be a hand-held device with the conversion layer (Continued)

arranged within a handle of the device to be gripped by a user when being carried.

19 Claims, 5 Drawing Sheets

(51) Int. Cl.
*G01N 23/09* (2006.01)
*G01T 1/20* (2006.01)

(52) U.S. Cl.
CPC . *G01N 2223/045* (2013.01); *G01N 2223/301* (2013.01); *G01N 2223/505* (2013.01)

(56) References Cited

U.S. PATENT DOCUMENTS

| | | | |
|---|---|---|---|
| 2005/0224719 | A1 | 10/2005 | Polichar et al. |
| 2010/0294415 | A1 | 11/2010 | Frank |
| 2011/0204243 | A1* | 8/2011 | Bendahan et al. ............ 250/367 |
| 2012/0018652 | A1* | 1/2012 | Yoder ..................... G01T 1/115 250/484.2 |
| 2012/0061580 | A1 | 3/2012 | Kline et al. |

FOREIGN PATENT DOCUMENTS

| | | |
|---|---|---|
| WO | WO2004/109331 | 12/2004 |
| WO | WO2011/087861 | 7/2011 |
| WO | WO2012/007734 | 1/2012 |
| WO | WO 2012/146415 | 11/2012 |

OTHER PUBLICATIONS

A Novel Neutron Multiplicity Detector Using Lithium Fluoride and Zinc Sulphide Scientillator, John C. Barton, Christopher J. Hatton and John E. McMillan Dept. of Physics, Birkbeck College, Univ. of London, Malet Street, London, WC1E 7HX, UK; Dept. of Combined Studios, Univ. of Leeds, Leeds LS2 9JT, UK; Dept. of Physics, Univ. of Leeds, Leeds LS2 9JT, UK; Received May 17, 1991, in Final Form Aug. 1, 1991; 0954-3899/91/121885 + 15 $03.50 @ 1991 IOP Publishing Ltd; pp. 1885-1889; J. Phys. G: Nucl. Part. Phys. 17 (1991) 1885-1899. Printed in the UK.

A Compact Neutron Detector Based on the Use of SiPM Detecto, Mark Foster and David Ramsden Member, IEEE Nuclear Science Symposium Conference Record (2008); pp. 1-5.

A Neutron Detector Using Silicon Pin Photodiodes for Personal Neutron Dosimetry, Takahiko Aoyama, Yasushi Oka, Kiyonari Honda and Chizuo Mori; Dept. of Nuclear Engineering, Nagoya Univ. Nagoya 464-01 Japan; Nuclear Instruments and Methods in Physics Research A314 (1992); pp. 590-594; Section A, vol. 314, Issue 3, 0168-9002/92/$05.00@1992—Elsevier Science Publishers B.V. All Rights Reserved.

Radseeker Handheld Rediation Detector and Identifier, Smiths Detector; Radseeker; pp. 1-3; http://www.smithsdetector.com/en/products-solutions/radiation-detection/56-radiation: Feb. 19, 2014.

Gamma Discrimination in Pillar Structured Thermal Neutron Detectors, Q.Shao, R.P. Radev, A.M. Conway, L.F. Voss, T.F. Wang, R.J. Nikolic, N. Deo, C.L. Cheung; Mar. 30, 2012; SPIE Defense Security and Sensing 2012; Baltimore, MD, U.S. Apr. 23, 2012 Through Apr. 27, 2012; LLNL-Proc-543492; pp. 1-11.

Design Considerations for Thin Film Coated Semiconductor Thermal Neutron Detectors-I: Basics Regarding Alpha Particle Emitting Neutron Reactive Films, D.S. McGregor, M.D. Hammig, Y.H. Yang, H.K. Gersch, R.T. Klann; Dept. of Mechanical and Nuclear Engineering, Kansas State Univ. 318 Rathbone Hall, Manhattan, KS 66506, USA, Dept. of Nuclear Engineering and Radiological Sciences, Univ. of Michigan, Ann Arbor, MI 48109, USA; 105 Briarwood Drive, Versailles, KY 40383-9142, USA; Argonne National Laboratory. 9700 South Cass Avenue, Building 362, Room B-113, Argonne, IL 60439, USA; Received May 17, 2002, Received in Revised Form Nov. 20, 2002; Accepted Nov. 22, 2002; Available on Line at www.sciencedirect.com; Nuclear Instruments & Methods in Physics Research; pp. 272-308.

* cited by examiner

NEUTRON DETECTOR AND METHOD FOR DETECTING NEUTRONS

The present invention relates generally to apparatus and methods for neutron detection.

One of the more challenging tasks that have been set for radiation detectors is the reliable detection of nuclear weapons and special nuclear materials which may be concealed in cargo crossing at international borders. Whilst approximately 1 to 2% of all cargo vehicles carry innocent radioactive materials only around one in 10,000 of these are found to be carrying a neutron source. In these cases, the neutrons could be generated by legitimate cargo related to the tools used in the oil and gas exploration industry, sources used in soil moisture gauges or in some radiography applications, for example. The rarity of such cargo means it is generally considered practical to examine in detail any cargo found to contain such a source to confirm its nature and origin.

The neutron energy spectra generated by mixing intense alpha-particle emitters such as Americium-241 with Lithium or a Plutonium-238 source with Beryllium or that from fissile materials, extend into the MeV energy range. Since the most effective means for the detection of neutrons is to use materials which have a high cross-section for thermal neutrons, it is normal practice to moderate the energy of the incident neutrons using such low density, hydrogenous materials such as polyethylene. From this, it is apparent that a thermal neutron detector alone may not provide an efficient means for a detector of either innocent or contraband neutron sources, due to the high neutron energies of these sources.

For many years the most widely used detector for thermal neutrons has been based on the use of $^3$He gas proportional counters. These high-pressure gas counters (~1-3 bar) are typically surrounded by 3-5 cm of a moderating material such as high-density polyethylene. These detectors are still available in sizes that range from 12 to 50 mm in diameter and from 100 to 2000 mm long [1]. However, in recent years, the development of a replacement for the use of $^3$He proportional counter systems in view of the growing shortage of this material has been carried out. These systems all use a similar approach to that described first by Barton et al. [2] in which an intimate mixture of $^6$LiF and ZnS:Ag is used to provide both a neutron-capture mechanism and a scintillation counter material. Slow neutrons interact in the $^6$Li$_3$ nucleus to produce a triton and an alpha particle. For this reaction, the Q-value is 4.78 MeV (i.e. $^6$Li$_3$+$^1$n$_0$→$^3$H$_1$+$^4$α$_2$+ 4.78 MeV). Since there are no gaseous lithium compounds readily suitable for use in proportional counters, practical Lithium-based neutron detectors have largely been based on scintillation counter designs. The ranges of the alpha particle and the triton are both very limited and so the $^6$LiF and ZnS may be combined in a finely powdered form in order to maximise the brightness of the scintillation flash that is generated when a neutron interacts in a detection screen comprising an intimate mixture of $^6$LiF and ZnS:Ag. Similar detectors can also be fabricated to make use of a similar neutron-capture process in $^{10}$Boron though the reaction $^{10}$B$_5$+$^1$n$_0$→$^7$Li$_3$+$^4$α$_2$+2.78 MeV.

Various implementations using $^6$LiF and ZnS type detectors have been described. These differ in implementation regarding the design of a light-guide used to transport scintillation light to a photo-detector and in the electronic techniques used to distinguish neutron events from the much larger number of gamma-ray induced events that are present in some extreme environments in which the neutron detector must operate.

One known example is described in US 2010/0294415 [7] and uses wavelength-shifting fibres embedded in a LiF/ZnS matrix with a combination of rise-time fall-time, pulse duration and amplitude discrimination used to distinguish between neutrons and gamma-rays. A further example is described in WO 2004/409331 [8] which uses LiF2nS detection screens sandwiched between scintillating plates. A similar example is described in US 2005/0224719 [9] which uses LiF/ZnS detection screens sandwiched between multiple planar light-guides. US 2011/0204243 [10] also describes sandwiching a detection screen, but between two polyvinyltoluene (PVT) scintillator plates, and also describes pulse-shape discrimination between gamma-ray events in the plastic and the longer wavelength-shifted neutron signal. WO 2012/007734 [12] describes PVT wavelength-shifting paddles clad with LiF/ZnS:Ag screens, where gamma-ray events and neutron signals are distinguished by digitally analysing each event.

Most of the neutron detectors described in the above references have found application in the field of radiation portal monitors for which a $^3$He detector-replacement market is beginning to develop. There is, however, a range of alternative $^3$He-free detection systems suitable for application in the field of smaller systems. These can be summarised as follows:

- A compact neutron detector based on the use of a LiI(Eu) scintillation crystal viewed by a silicon photomultiplier [3]. The area of the crystal in this example is relatively small, typically a few cm$^2$, and could not typically be extended simply because the boule size is limited to around 30 mm diameter and because the material is very deliquescent. A light-guide is used to match the crystal scintillator to the photo-detector;
- A 1 cm$^2$ LiI(Eu) crystal viewed by a PIN photodiode [4];
- A PIN diode close to a gadolinium foil [5];
- A thermal neutron detector constructed by filling perforations in a silicon sensor with a $^6$Li rich material. In operation, the fragments produced, following the capture of a neutron by the lithium nucleus, generate ionisation in the silicon [6]; and
- A silicon detector doped with $^{10}$B [13].

The detectors described above have a sensitive area of one or two square centimeters, which is much less than the previous described LiF/ZnS examples which might have sensitive areas two or three orders of magnitude greater. Because of the relatively small sensitive areas of these small-scale devices they have a corresponding reduction in sensitivity. In some respects this means such detectors may not be suitable in some circumstances, for example where greater sensitivity combined with portability is desired.

Therefore, there is a desire to provide for a neutron detector that is compact yet capable of detecting neutrons from high-energy neutron sources.

SUMMARY OF THE INVENTION

In accordance with a first embodiment of the invention there is provided an apparatus comprising a neutron detector, the neutron detector comprising: a conversion layer comprising a mixture of a neutron absorbing material and a scintillation material; a light-guide arranged to receive photons emitted from the scintillation material; and a photodetector optically coupled to the light-guide and arranged to detect photons generated as a result of neutron absorption events in the conversion layer; wherein the apparatus is adapted to be carried by a user and the conversion layer is positioned within the neutron detector such that when the apparatus is being carried by a user in normal use neutrons are absorbed in the conversion layer after passing through the user.

Thus, a neutron detector is provided in which the neutron absorbing component of the detector, the conversion screen, is arranged within the detector so as to benefit from the moderating effects of a user's body, thereby improving sensitivity with respect to high-energy neutrons in a manner which does not rely on a dedicated moderator material within the neutron detector, thereby helping provide a neutron detector in a compact format.

In accordance with some embodiments the light-guide is a wavelength shifting light-guide arranged to receive photons emitted from the scintillation material of the conversion screen and generate wavelength-shifted photons therefrom.

In accordance with some embodiments the apparatus may further comprise a gamma-ray detector including a gamma-ray scintillator, for example a plastic gamma-ray scintillator such as PVT, which is arranged relative to the conversion screen to provide a moderating function for neutrons passing through the gamma-ray scintillator.

In accordance with some embodiments the conversion layer is positioned adjacent an external wall of a housing of the neutron detector.

In accordance with some embodiments the conversion layer is positioned within the neutron detector so as to be adjacent a user when the apparatus is being carried by the user in normal use.

In accordance with various embodiments of the invention the apparatus may be adapted to be carried in various different ways. For example, in some example embodiments the apparatus may comprise a backpack in which the neutron detector is located. In accordance with some embodiments the conversion layer may be located adjacent a surface of the backpack arranged to be adjacent a user's back when the apparatus is being carried by the user in normal use. In accordance with some embodiments the apparatus may comprise a garment in which the neutron detector is located. In accordance with some embodiments the apparatus may comprise a clip for attaching the apparatus to a users garment. In accordance with some embodiments the neutron detector may be configured to be located in a pocket of a garment worn by a user.

In accordance with some embodiments the apparatus may comprise a handle configured to be held by a user when the apparatus is being carried by the user in normal use, and wherein the conversion layer is located within the handle.

In accordance with some embodiments the photodetec or may comprise one or more silicon photomultiplier(s).

In accordance with some embodiments the apparatus may further comprise a neutron moderating material arranged such that neutrons are absorbed in the conversion layer after passing through the neutron moderating material.

In accordance with some embodiments the conversion layer and the light-guide may be arranged together to form a neutron detector element in the form of a sheet. The neutron detector element may have surfaces comprising two faces separate by edges, the faces having a larger area than the edges. Furthermore, a face of the neutron detector element may be arranged to be generally parallel with a portion of a user against which the neutron detector element is adjacent when the apparatus is being carried by the user in normal use.

In accordance with some embodiments the neutron detector element may have a thickness which is less than a value selected from the group comprising 10 mm, 9 mm, 8 mm, 7 mm, 6 mm, 5 mm, 4 mm, 3 mm, 2 mm and 1 mm. Furthermore, a face of the neutron detector element may have a characteristic extent in a first direction which is less than a value selected from the group comprising 200 mm, 190 mm, 180 mm, 170 mm, 160 mm, 150 mm, 140 mm, 130 mm, 120 mm, and 100 mm, 90 mm, 80 mm, 70 mm, 60 mm, 50 mm, 40 mm, 30 mm, 20 mm, and 10 mm. Furthermore still, a face of the neutron detector element may have a characteristic extent in a second direction orthogonal to the first direction which is less than a value selected from the group comprising 200 mm, 190 mm, 180 mm, 170 mm, 160 mm, 150 mm, 140 mm, 130 mm, 120 mm, and 100 mm, 90 mm, 80 mm, 70 mm, 60 mm, 50 mm, 40 mm, 30 mm, 20 mm, and 10 mm.

In accordance with another aspect of the invention there is provided a method for detecting neutrons, comprising the steps of: providing a neutron detector comprising: a conversion layer comprising a mixture of a neutron absorbing material and a scintillation material; a light-guide arranged to receive photons emitted from the scintillation material; and a photodetector optically coupled to the light-guide and arranged to detect photons generated as a result of neutron absorption events in the conversion layer, wherein the conversion layer is positioned within the neutron detector such that when the neutron detector is being carried by a user in normal use neutrons are absorbed in the conversion layer after passing through the user; and wherein the method further comprises a user carrying the neutron detector and detecting photons generated as a result of neutron absorption events in the conversion layer.

It will be appreciated that features and aspects of the invention described above in relation to the first and other aspects of the invention are equally applicable to, and may be combined with, embodiments of the invention according to other aspects of the invention as appropriate, and not just in the specific combinations described above.

BRIEF DESCRIPTION OF THE DRAWINGS

For a better understanding of the invention and to show how the same may be carried into effect reference is now made by way of example to the accompanying drawings in which.

DETAILED DESCRIPTION

It is apparent that known neutron detector techniques might not provide an efficient means for the detection of either innocent or contraband neutron sources in a compact format apparatus. The inventors have recognized that a neutron detector for detecting relatively high energy (non-thermal) neutrons may be provided in a compact format by exploiting the moderating properties of material which is not part of the detector itself, but which is nonetheless in the vicinity of the detector when in normal use. More particularly, in accordance with embodiments of the invention a neutron detector is provided which is configured to make use of the moderating effects of a user's body when the detector is in normal use.

The inventors have found that this approach can provide for a reliable degree of detection sensitivity for non-thermal neutrons without needing to provide dedicated moderating material which might otherwise increase the mass of a stand-alone neutron detector rendering it less portable. For example, in accordance with one embodiment a neutron detector may be incorporated within a handle portion of a detector to exploits the moderating effects of the operator's hand on the incident, fast (i.e., high energy) neutron flux whilst the instrument is in use and, to some extent, the greater mass of the user's body. In this way the sensitivity of the instrument when it is in normal use can be enhanced as compared to its "on the bench" sensitivity. Similarly, in accordance with other embodiments of the invention a wearable neutron detection system or back-pack may be provided. In such cases the neutron detector would normally be located so as to be in close contact with or proximal to the body of the user. Thus, a neutron detector which may take advantage of the neutron moderating properties of the human body, which because it contains a large proportion of water provides an efficient neutron moderator material, in accordance with embodiments of the invention can significantly enhance the effective sensitivity of a simple, light-weight neutron detector.

Figure 1:
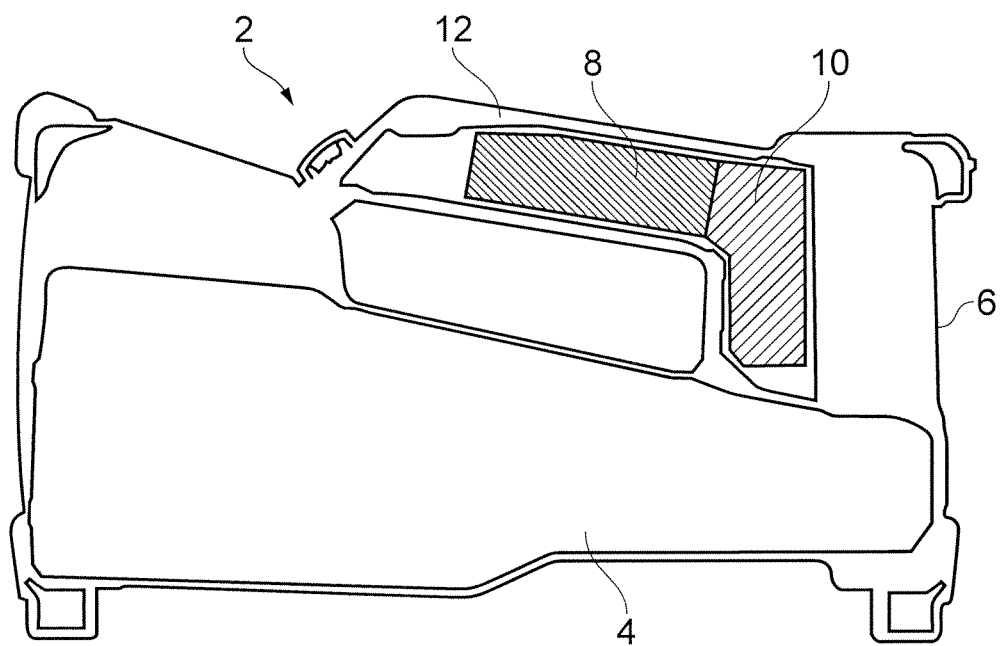
FIG. 1 illustrates schematically in cross section an apparatus according to an embodiment of the invention.

FIG. 1 illustrates schematically in cross section an apparatus 2 according to an embodiment of the invention. The apparatus 2 is based generally around a Smiths Detection Radseeker handheld radiation detector and identifier for detecting and identifying gamma-rays [12]. The apparatus 2 includes a commercial Sodium Iodide (CS) and Lanthanum Bromide (CL) detector package 4, contained within a portable, handheld, enclosure 6. The CS/CL detector package 4 includes a power source and a processor/controller (not shown). The Smiths Detection Radseeker hand-held gamma-ray spectrometer is typically used to search cargo at ports and borders for illicit radio-active materials.

However, in accordance with embodiments of the invention the conventional Radseeker handheld radiation detector is modified to incorporate a neutron detector. Thus, the apparatus 2 represented in FIG. 1 further comprises a neutron detector 8 and associated controller/processing electronics 10. The controller 10 may also include a power source (not shown) or may be coupled to the power source of the CS/CL detector package 4. The neutron detector 8 is arranged within the handle 12 of the enclosure 6, more specifically, the neutron absorbing sensitive part of the neutron detector, as discussed further below, is arranged within a portion of the apparatus which is gripped by a user when holding the apparatus in normal use.

In accordance with this example embodiment of the invention, the neutron-sensitive element of the neutron detector is based around a sheet-like neutron absorbing layer, which might also be referred to as a conversion screen, discussed further below.

Figure 2:
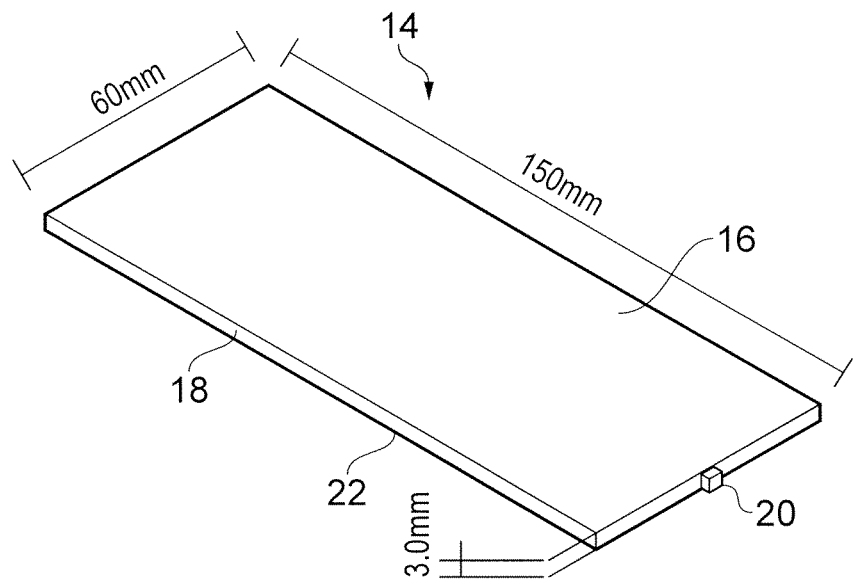
FIG. 2 illustrates schematically a neutron detection element of the neutron detector illustrated in FIG. 1.

Thus, FIG. 2 illustrates schematically a neutron detection element 14 of the neutron detector 8 illustrated in FIG. 1. The neutron detection element 14 has a generally low-profile (tile-like) layered structure. The neutron detection element 14 includes a conversion layer or screen 16 placed in close optical contact with a wavelength-shifting light-guide 18 in the form of a plastic scintillator plank (or sheet). The light-guide 18 is coupled to a photodetector 20. In this example, the neutron detector 8 further comprises a second optional conversion screen or layer 22 which is arranged on an opposing face of the wavelength-shifting light-guide 18. The second conversion screen 22 is also placed in close optical contact with a wavelength-shifting light-guide 18. Output signals from the photodetector 20 are passed to the controller/processor 10, illustrated in FIG. 1. In this example, the neutron detection element 14 is generally sheet-like with an overall length of around 150 mm, a width of around 60 mm and with a thickness of around 3 mm. It will however be appreciated that in other examples different characteristic scales of detector may be appropriate.

Each of the conversion layers 16, 22 comprise a finely powered mixture of a neutron absorbing material and a scintillation material mounted on a respective substrate. The substrate of the conversions layers 16, 22 may be a polyester sheet with a reflective backing oriented to face the light-guide 18. The reflective backing may be affixed to the substrate or may comprise a separate element. Alternatively, or in addition, the substrate of the conversions layers 16, 22 may be translucent, e.g., Mylar or Melinex. The mixture of neutron absorbing material and scintillation material comprises powdered forms of each which are well-mixed in a resin binder and spread onto the substrate. e.g. in a layer perhaps around 0.1 to 0.5 mm thick, and left to set. In this example, the neutron absorbing material comprises $^6$Li enriched LiF. The scintillation material comprises ZnS(Ag). In other examples the neutron absorbing material may be based on or include other neutron-absorbing elements, e.g. a $^{10}B_2O_3$ mixture. Equally, in other examples the scintillation material may be based on/include other scintillation material, e.g. using pure CsI or yttrium aluminium perovskite (YAP) in powdered/granular form.

In this example the wavelength-shifting light-guide 18 comprises a sheet of wavelength-shifting plastic scintillator material, e.g. based on polyvinyltoluene (PVT) such as the EJ-280 materials available from Eljen Technology, Texas, USA.

The wavelength-shifting light-guide 18 may be in close optical contact with the respective conversion screens so that optical photons from the scintillation material in the conversion screens are readily coupled into the wavelength-shifting light-guide 18. However, in this example the conversion screens are in loose contact (as opposed to bonded contact) with the wavelength-shifting light-guide 18 such that they do not significantly disrupt total internal reflection processes within the wavelength-shifting light-guide 18. However, in other examples the conversion screens may be more closely bonded to the light guide 18. Indeed, in some cases the materials comprising the conversion screens (i.e. the neutron absorbing material and scintillation material) may be fixed directly to the light guide without any separate substrates. That is to say, the light guide 18 may itself comprise a substrate for the conversion screen(s).

The role of the neutron detection element 14 is to convert incident neutrons into light that may be detected by the photodetector 20. Thus, a neutron incident on the neutron detector 8 may be absorbed by the neutron absorbing material in one of the conversion screens of the neutron detection element 14 by interacting with one of the $^6$Li nuclei. This reaction ($^6$Li$_3$+$^1$n$_0$→$^3$H$_1$+$^4$α$_2$+4.78 MeV) results in reaction fragments that readily excite the inter-mixed scintillation material ZnS(Ag), causing it to radiate photons. These photons may be referred to as neutron interaction photons and follow the emission spectrum of the ZnS(Ag) scintillator, which has a peak at a wavelength of around 450 nm. The neutron interaction photons are emitted in all directions. Since the conversion layers 16, 22 are relatively thin, for most interaction sites the light-guide presents a solid angle of around $2\pi$ such that close to half of the photons from the neutron interaction that escape the respective conversion layers 16, 22 of the neutron detection element 14 enter the light-guide 18. Furthermore, there is a chance that some of the remaining half of photons from the scintillation material (i.e. those initially travelling away from the respective light-guides) may also enter the light-guide following reflection from the substrates of the respective conversion screens. Thus a relatively large fraction of the neutron-induced photons from the scintillation material may enter the light-guide.

Figure 3:
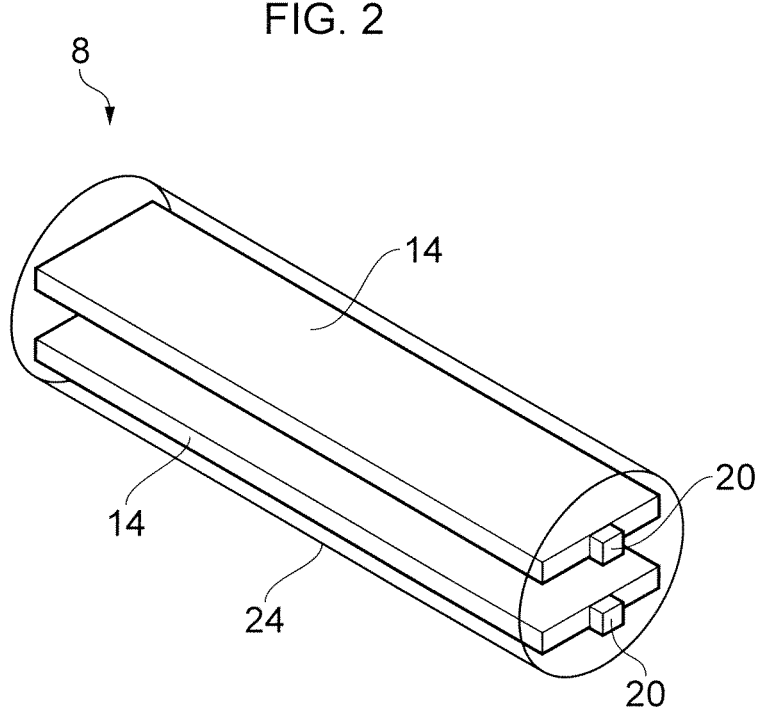
FIG. 3 illustrates schematically the neutron detector illustrated in FIG. 1.

FIG. 3 illustrates schematically the neutron detector 8 illustrated in FIG. 1. The neutron detector 8 in this example comprises two of the neutron detection elements 14 illustrated in FIG. 2 with their associated photodetectors 20. The neutron detector 8 further includes a tubular sleeve 24 of neutron moderating material generally surrounding the neutron detection elements 14. The sleeve 24 is generally elongate having a similar length to the neutron detection elements 14 and a diameter similar to the width of the neutron detection elements 14. The moderating material in this example is HDPE having a thickness of around 1, but in alternative embodiments other materials might be used, for example, PVT.

The dimensions of the light-guides 18 may be selected so as to match those of the conversion screen(s) and a selected photo-detector (or vice versa) to help improve the overall light-collection efficiency of the neutron detector. The conversion screen(s) 16, 22, together with an associated wavelength-shifting component (light guide) 18 can thus be dimensioned to provide a slim, light weight detector that can be mounted, in this example, within the handle of an instrument. Thus, when the instrument 2 is in normal use being held by a user, the user's hand grips the handle portion of the housing 6 so as to (at least partially) surround the neutron detection element 14, thereby providing a moderating function with respect to incoming neutrons, thereby increasing the detection sensitivity of the neutron detector to the incoming neutron flux. Thus while some moderating material may be provided within the handle 12 for the neutron detector 8 of the apparatus 2 illustrated in FIG. 1, the inventors have found a significant improvement in sensitivity can be achieved when a user is grasping the handle because of the additional moderating effects of the users body. It has been found that the sensitivity of the neutron detector 8 may be expected to improve by a factor of approximately two when the handle 12 is grasped in the hand of the/user operator.

As regards the photodetector 20, a solid-state device, such as a silicon photodiode, avalanche photodiode or silicon photomultiplier (SiPM) may be used for the neutron detectors described herein. Individual silicon photo-multipliers may typically have dimensions of 3×3 mm and are sometimes pre-fabricated into arrays having a larger detection area. The photodetector 20 may comprise an individual silicon photomultiplier or a combined array of silicon photomultipliers, for example in an array configured to conform to an edge of the light guide to which they are coupled. Recently, larger silicon photomultipliers have started becoming available, for example individual devices having dimensions of 6×6 mm have become available and these may be used in some cases. However, for other embodiments of the invention there may be a desire to minimise the mass and dimensions of the neutron detector assembly to an extent that a 3×3 mm silicon photomultiplier may be preferred and matched to the thickness of the wavelength-shifting material of the light-guide 18. In the examples illustrated in FIGS. 2 and 3 the respective photodetectors 20 are assumed to be single 3×3 mm silicon photomultipliers coupled to the light-guide 18.

The single-photon counting capability of a silicon photomultiplier and its speed can offer advantages for helping to identify neutrons in the presence of an intense flux of gamma-rays.

Figure 4:
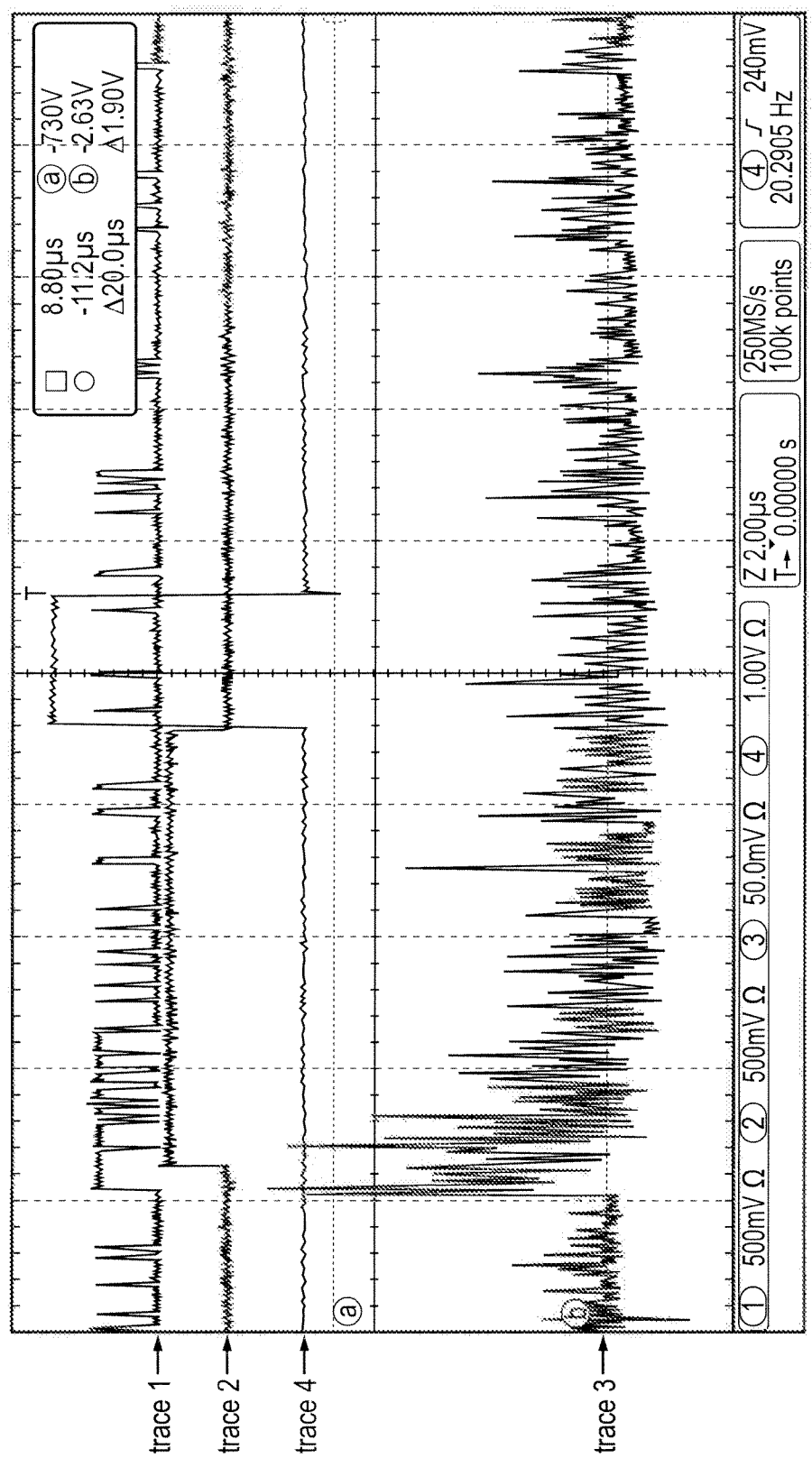
FIG. 4 is graph used to illustrate how event selection may be performed in accordance with an embodiment of the invention.
Figure 5:
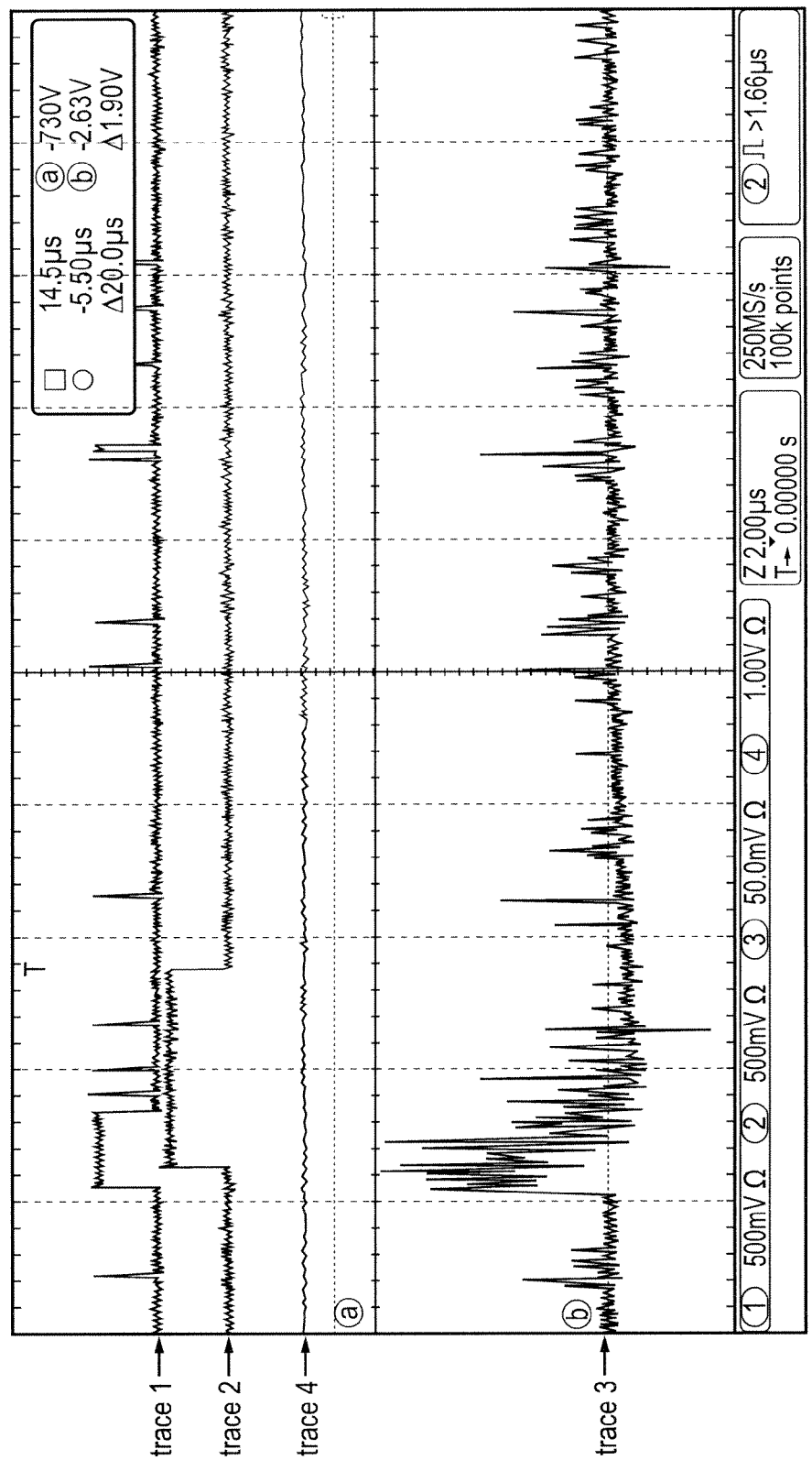
FIG. 5 is a graph used to illustrate a gamma-ray interaction in the detector in accordance with an embodiment of the invention.

For a neutron detector design in accordance with the principles set out above and in which one or more silicon photo-multipliers are optically coupled to the edge of a 3 mm thick wavelength-shifting plastic sheet having dimensions of 60×150 mm, the raw signal from the SiPM for a neutron absorption event and a gamma-ray interaction event in the neutron detector are schematically illustrated in the respective lower traces (labelled trace 3 in both cases) of the respective graphs illustrated in FIGS. 4 and 5. It may be noted the 'richness' (e.g. in terms of the density of separately identifiable peaks) of these signals is greater than generally seen in other LiF/ZnS:Ag systems based on the use of wavelength-shifting fibres.

The neutron detector 8 is coupled to a controller/processor 10 that receives the signals outputted by the photodetector 20, such as the signals representing the respective lower traces of FIGS. 4 and 5. Event selection (i.e. a determination as to whether or not a given signal is to be taken as being associated with a neutron detection event) as performed by the controller 10 in accordance with some embodiments is now described with reference to FIGS. 4 and 5. The processor includes various component blocks including a discriminator, one or more counters and a clock (not shown). As is conventional, these functional elements of the controller may be provided as hardware blocks or part of a programmed processor of a general purpose computer or a specifically configured ASIC.

FIG. 4 represents a series of traces (labelled trace 1, 2, 3 and 4) for illustrating how event selection may be performed. As noted above, the raw photodetector output for a typical neutron event is shown in trace 3 (lower trace) of FIG. 4. As is apparent from the figure, this trace comprises a number of separately identifiable peaks. FIG. 5 is similar to FIG. 4, but shows corresponding traces associated with a gamma-ray detection event instead of a neutron detection event. As also noted above, the raw photodetector output for a typical gamma-ray event is shown in trace 3 (lower trace) of FIG. 5. As is apparent from FIGS. 4 and 5, the respective raw photodetector output signals for the neutron detection event and the gamma-ray detection event are in many respects similar in appearance with each comprising a number of separately identifiable closely-spaced peaks.

In accordance with certain embodiments of the invention the controller 10 is configured to process the raw photodetector output signals from the photodetector 20 (such as represented by trace 3 in each of FIGS. 4 and 5) as follows.

When the raw photodetector signal exceeds a preset discrimination level, a corresponding discriminator output is gated with a 20 MHz clock to generate a gated pulse train. The gated pulse trains for the neutron detection event (FIG. 4) and the gamma-ray detection event (FIG. 5) are identified by the label trace 1 in the respective FIGS. 4 and 5. It may be noted for each of FIGS. 4 and 5 there are some pulses seen in trace 1 prior to the initiation of the main group of peaks associated with the detection event in trace 3. These events may be attributed to noise in the SiPM photodetector or low-level background gamma radiation detection events.

The processor is configured to determine when the output from the discriminator remains high for more than a pre-defined number of clock pulses, in this example 6 clock-pulses. When this occurs a second logic level is triggered to switch, for example to go from low to high. Representations of this second logic level for the neutron detection event (FIG. 4) and the gamma-ray detection event (FIG. 5) are identified by the label trace 2 in the respective FIGS. 4 and 5.

The second logic level remains high until a period corresponding to a pre-determined time, in this example 1 µs, has passed without there being a falling edge transition on the gated pulse train represented in trace 1 in the respective FIGS. 4 and 5. When the second logic level switches from high to low (or low to high depending on implementation polarity), the controller determines how long the second logic level remained high, for example in terms of the number of clock-pulses for which the second logic level of trace 2 remained high.

If the number of clock-pulses for which the second logic level or trace 2 remains high exceeds a preset threshold, for example 50, the event is deemed to be associated with a neutron interaction event whereas if the number of clock pulses for which the second logic level remains high is less than this preset digital threshold, the event is deemed not to be associated with a neutron interaction event.

Thus, when the second logic level remains high for longer than a predefined period (e.g. corresponding to the preset digital threshold number of clock pulses) a logic output associated with the nuclear detector is set to transition (e.g. to switch from low to high) for a period. Thus, a pulse on the logic output may be taken to indicate a neutron detection event. The logic output corresponding to the neutron detection event (FIG. 4) and the gamma-ray detection event (FIG. 5) are identified by the label trace 4 in the respective FIGS. 4 and 5. Thus, it can be seen in FIG. 4 that the logic output switches to high on the downward transition of trace 2 (because trace 2 remained high for greater than the preset number of clock pulses discussed above) to indicate a neutron detection event. However, and in contrast, the logic output does not switch on the downward transition of trace 2 in FIG. 5 (because trace 2 did not remain high for greater than the preset number of clock pulses discussed above).

In some example embodiments the neutron detector may be configured to output a gamma-ray detection pulse if a trace corresponding to trace 2 in FIGS. 4 and 5 remains high for a period which is less than the predetermined time associated with a neutron detection event, but for greater than a smaller threshold period. This may allow the detector to distinguish gamma-ray detection events from noise events. Thus, depending on the duration for the switch in trace 2 from its quiescent state, the neutron detector may output a signal indicating a determination of a neutron detection event, a signal indicating a determination of a gamma-ray detection event, or no signal at all.

The above processing represents one way in which the inventors have found signals from the photodetector of a neutron detector in accordance with an embodiment of the invention may be processed to reliably identify neutron detection events. It will, however, be appreciated that there are many other signal processing techniques that may be applied to the photodetector output signal, for example in accordance with conventional signal processing techniques in the art. Furthermore, it will be appreciated that when an approach based on the above-described technique is adopted, the specific values mentioned may be varied according to the implementation at hand. In general, it may be expected that suitable values for the various parameters associated with the processing may be configured based on an empirical analysis using calibration sources, for example.

As has been noted above, neutron detectors in accordance with embodiments of the invention are adapted such that the neutron-absorbing component of the neutron detector, i.e. the conversion screen(s) in the examples discussed above, are located when the detector is being carried in normal use in such a way so as to benefit from the neutron moderating properties of the operator's body. This is achieved in the example illustrated in FIG. 1 by accommodating a neutron detector in the handle of an instrument that the operator will be carrying in the course of their duties.

A further embodiment of the invention may, for example, be based on the arrangement illustrated in FIG. 3, comprising two neutron detection elements arranged within a cylindrical enclosure, which may also form an outer moderating sleeve 24. Such an arrangement may be used as a simple pocket-mounted neutron detector, which may also include a power source and isotope-identification processor coupled to the photodetectors 20. For example, the pocket mounted neutron detector could be sized to be accommodated within a standard pocket of user's clothing/garments. In other examples an apparatus comprising a neutron detector in accordance with an embodiment of the invention may be provided with a clip or other attachment mechanism to facilitate its attachment in close proximity to a user's body.

Furthermore, it is envisaged that the arrangement illustrated in FIG. 3 could be combined into a gamma-ray and neutron detection system along with radio communication, an isotope-identification processor and a power source that could be mountable on a user's belt (or otherwise carried) in another embodiment of the invention. In this configuration the thermalized neutrons from the wearer's body when the user is in the vicinity of a high energy neutron source would interact in the LiF/ZnS conversion screen and lead to triggering of a neutron detection event as discussed above. The radio communication component of the neutron detector may be configured to transmit an indication of such a detection (or a plurality of such detections occurring at a pre-defined rate) to a remote processing or storage unit for handling as appropriate having regard to the implementation at hand. For example, the wearer may be an operator at a port, and the transmission of an indication of a neutron detection event to a remote station may result in cargo near to the user at the time of the detection event being diverted for further investigation. In another case, the wearer may be a scientist working in a laboratory environment and the detection of neutrons above a defined rate may be used to trigger an alarm warning of a possible excess exposure to radiation.

A further embodiment of the invention may include a larger area detector than those discussed above, for example comprising four detector panels or neutron detection elements similar to those illustrated in FIG. 2, arranged to provide a total area of around 0.06 to 0.08 m$^2$ (for example, each detector panel may be 0.06 m by 0.3 m) and may be mounted in or on the surface of a garment worn by a user, for example a high-visibility type jacket. In some cases one or more detector panels could be mounted on the front or forward facing portion of a garment and one or more detector panels could be mounted in the back or rearward facing portion of the jacket. This arrangement could thus provide an element of directional information (i.e. depending on which neutron detector(s) are associated with detection events) that could aid the location of the neutron source. For example neutrons coming from in front of the user will typically be moderated in the front portion of the user's body and so lead to a greater number of neutron detections associated with the neutron detection elements arranged on the front-facing portion of the jacket, as compared to the back-facing portion of the jacket (because of their respective proximities to where in the user's body the neutrons are moderated). Similarly, a neutron source located behind the user can be expected to give rise to a greater number of neutron detection events associated with the neutron detection elements arranged on the back-facing portion of the jacket. It will be appreciated that a power source and processing electronics could also be included in the jacket or garment to be worn by the user.

Figure 6:
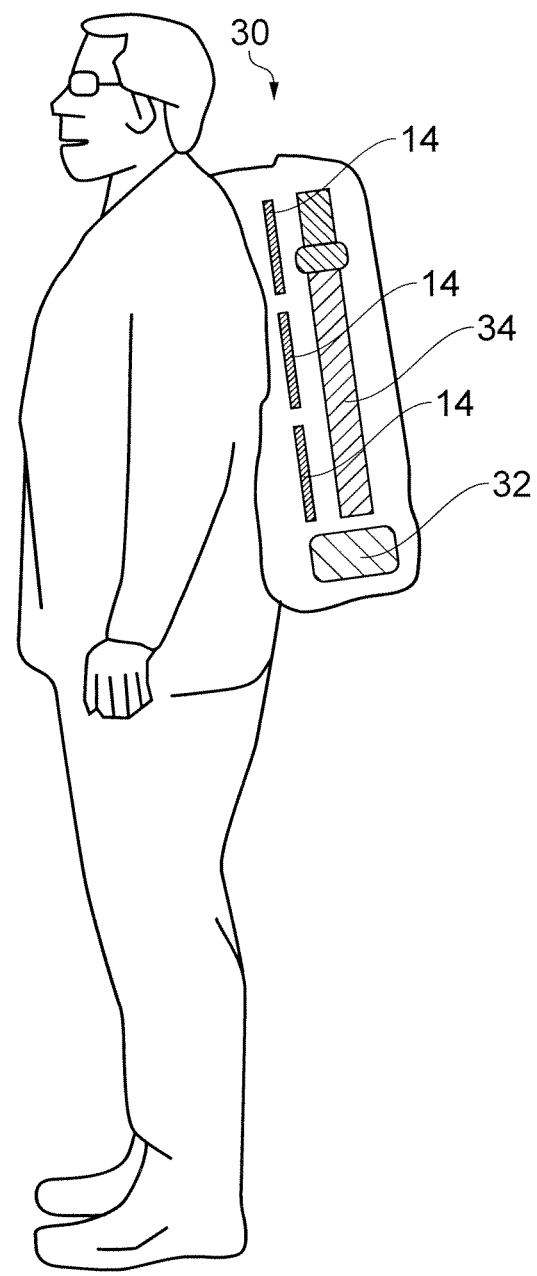
FIG. 6 illustrates schematically an apparatus according to another embodiment of the invention.

FIG. 6 illustrates schematically an alternative neutron detector provided in the form of a back-pack 30 or bag that can be carried by a user, preferably on their back, using one or more straps. In the example shown in FIG. 6, the bag includes a number (three in this example) of detector panels/neutron detection elements 14, similar to those illustrated in FIG. 2, to provide a relatively large sensitive-area in a plane that is proximally adjacent and substantially parallel to the back of the operator when the backpack is being carried in normal use. A processor and power source 32 are also provided in the bag 30. This example also includes a gamma-ray spectrometer of known configuration, for example, a 50 mm thick polyvinyltoluene scintillation counter provided to detect gamma radiation and generate spectra therefrom. In further examples, the scintillation counter of an associated gamma-ray detector may also include a conversion screen, such as described above, that is arranged between the user (or a back support of the bag) and a polyvinyltoluene scintillation based counter. Neutrons coming toward the rear of the user may thus pass through the polyvinyltoluene scintillation counter, which will act as a moderator, and may be thermalized in the associated conversion screen. The neutron detection elements 14 will work in the same manner as described for the panels arranged in the rearward facing portion of a jacket, described above.

Alternatively, the gamma-ray spectrometer may be replaced by a second neutron detector screen positioned in the bag and which comprises a wavelength-shifting plastic sheet (e.g., a 25-35 mm thick polyethylene sheet) and a conversion screen arranged on a forward (with respect to the user or bag when worn by a user on their back) facing surface of the plastic sheet. The second detector may be arranged in a bag so that the neutron detector screens 14 are arranged between the second screen and the back support of the bag. Accordingly, neutrons coming toward the rear of the user will thus pass through the polyethylene sheet of the second screen and reduced in energy and may thermalize in the conversion screen of the second screen.

Thus in accordance with some embodiments of the invention an apparatus comprising a neutron detector is described. The neutron detector comprises a conversion layer comprising a mixture of a neutron absorbing material and a scintillation material; and a photodetector optically coupled to the conversion layer and arranged to detect photons generated as a result of neutron absorption events in the conversion layer; wherein the apparatus is adapted to be carried by a user and the conversion layer is positioned within the neutron detector such that when the apparatus is being carried by a user in normal use neutrons are absorbed in the conversion layer after passing through the user such that the user's body provides a neutron moderating effect. In some cases the apparatus may be carried in association with a backpack or clothing worn by a user, for example, the neutron detector may be sized to fit in a pocket. In other cases the apparatus may be a hand-held device with the conversion layer arranged within a handle of the device to be gripped by a user when being carried.

In the interest of brevity the description of embodiments of the invention provided above has focused on those aspects of the neutron detector which differ from conventional neutron detectors and neutron detection techniques. It will of course be appreciated that operational aspects of the neutron detector which are not specifically described herein may be implemented in accordance with conventional techniques in the art.

While the invention is described herein by way of example for several embodiments and illustrative drawings, those skilled in the art will recognize that the invention is not limited to the embodiments or drawings described. It should be understood, that the drawings and detailed description thereto are not intended to limit the invention to the particular form disclosed, but on the contrary, the intention is to cover all modifications, equivalents and alternatives falling within the spirit and scope of the present invention. The headings used herein are for organizational purposes only and are not meant to be used to limit the scope of the description. As used throughout this application, the word "may" is used in a permissive sense (i.e. meaning "might") rather than the mandatory sense (i.e., meaning "must"). Similarly, the words "include", "including", and "includes" mean including, but not limited to.

REFERENCES

[1] http://www.Indinc.com/products/category/38/
[2] J C Barton et al, Journal of Physics G, Nuclear Particle Physics, 17, 1991, pages 1885-1899
[3] http://www.raesystems.com/products/neutronrae-ii
[4] M Foster and D Ramsden, IEEE Nuclear Science Symposium Conference Record (2008)
[5] A Takahiko, Nuclear Instruments and Methods in Physics Research, Section A, Volume 314, Issue 3, pages 590-594
[6] D S McGregor et al, Nuclear Instruments and Methods A500, 2003, pages 272-308
[7] US 2010/0294415
[8] WO 2004/109331
[9] US 2005/0224719
[10] US 2011/0204243
[11] WO 2012/007734
[12] http://www.smithsdetection.com/RadSeeker.php
[13] Nicolic et al "Pillar structured thermal neutron detector" Applied Physics Letters, 93 (13), (2008), p. 133502.

The invention claimed is:

1. An apparatus comprising a neutron detector, the neutron detector comprising:
   a conversion layer comprising a mixture of a neutron absorbing material and a scintillation material;
   a light-guide arranged to receive photons emitted from the scintillation material; and
   a photodetector optically coupled to the light-guide and arranged to detect photons generated as a result of neutron absorption events in the conversion layer;
   wherein the apparatus is adapted to be carried by a user and the conversion layer is positioned within the neutron detector such that when the apparatus is being carried by a user in normal use neutrons are absorbed in the conversion layer after passing through the user;

wherein the conversion layer and the light-guide are arranged together to form a neutron detector element having a thickness which is less than 10 mm.

2. The apparatus of claim 1, wherein the light-guide is a wavelength shifting light-guide arranged to receive photons emitted from the scintillation material of the conversion screen and generate wavelength-shifted photons therefrom.

3. The apparatus of claim 1, further comprising a gamma-ray detector comprising a gamma-ray scintillator arranged relative to the conversion screen to provide a moderating function for neutrons passing through the gamma-ray scintillator.

4. The apparatus of claim 1, wherein the conversion layer is positioned adjacent an external wall of a housing of the neutron detector.

5. The apparatus of claim 1, wherein the conversion layer is positioned within the neutron detector so as to be adjacent a user when the apparatus is being carried by the user in normal use.

6. The apparatus of claim 1, wherein the apparatus comprises a backpack in which the neutron detector is located.

7. The apparatus of claim 1, wherein the conversion layer is located adjacent a surface of the backpack arranged to be adjacent a user's back when the apparatus is being carried by the user in normal use.

8. The apparatus of claim 1, wherein the apparatus comprises a garment in which the neutron detector is located.

9. The apparatus of claim 1, wherein the apparatus comprises a clip for attaching the apparatus to a user's garment.

10. The apparatus of claim 1, wherein the neutron detector is configured to be located in a pocket of a garment worn by a user.

11. The apparatus of claim 1, wherein the apparatus comprises a handle configured to be held by a user when the apparatus is being carried by the user in a normal use, and wherein the conversion layer is located within the handle.

12. The apparatus of claim 1, wherein the photodetector comprises at least one silicon photomultiplier.

13. The apparatus of claim 1, wherein the apparatus further comprises a neutron moderating material arranged such that neutrons are absorbed in the conversion layer after passing through the neutron moderating material.

14. The apparatus of claim 1, wherein the conversion layer and the light-guide are arranged together to form a neutron detector element in the form of a sheet.

15. The apparatus of claim 14, wherein the neutron detector element has surfaces comprising two faces separate by edges, the faces having a larger area than the edges.

16. The apparatus of claim 14, wherein a face of the neutron detector element is arranged to be generally parallel with a portion of a user against which the neutron detector element is adjacent when the apparatus is being carried by the user in normal use.

17. The apparatus of claim 14, wherein a face of the neutron detector element has a characteristic extent in a first direction which is less than a value selected from the group comprising 200 mm, 190 mm, 180 mm, 170 mm, 160 mm, 150 mm, 140 mm, 130 mm, 120 mm, and 100 mm, 90 mm, 80 mm, 70 mm, 60 mm, 50 mm, 40 mm, 30 mm, 20 mm, and 10 mm.

18. The apparatus of claim 17, wherein a face of the neutron detector element has a characteristic extent in a second direction orthogonal to the first direction which is less than a value selected from the group comprising 200 mm, 190 mm, 180 mm, 170 mm, 160 mm, 150 mm, 140 mm, 130 mm, 120 mm, and 100 mm, 90 mm, 80 mm, 70 mm, 60 mm, 50 mm, 40 mm, 30 mm, 20 mm, and 10 mm.

19. A method of detecting neutrons, comprising the steps of: providing a neutron detector comprising: a conversion layer comprising a mixture of a neutron absorbing material and a scintillation material; a light-guide arranged to receive photons emitted from the scintillation material; and a photodetector optically coupled to the light-guide and arranged to detect photons generated as a result of neutron absorption events in the conversion layer, wherein the conversion layer is positioned within the neutron detector such that when the neutron detector is being carried by a user in normal use neutrons are absorbed in the conversion layer after passing through the user; and wherein the method further comprises a user carrying the neutron detector and detecting photons generated as a result of neutron absorption events in the conversion layer, and the conversion layer and the light-guide together have a thickness that is less than 10 mm.

* * * * *